(12) United States Patent
Kersey et al.

(10) Patent No.: US 7,602,952 B2
(45) Date of Patent: Oct. 13, 2009

(54) SCANNER HAVING SPATIAL LIGHT MODULATOR

(75) Inventors: Alan Kersey, South Glastonbury, CT (US); John A. Moon, Wallingford, CT (US)

(73) Assignee: Illumina, Inc., San Diego, CA (US)

( * ) Notice: Subject to any disclaimer, the term of this patent is extended or adjusted under 35 U.S.C. 154(b) by 639 days.

(21) Appl. No.: 11/281,937

(22) Filed: Nov. 16, 2005

(65) Prior Publication Data

US 2006/0139635 A1 Jun. 29, 2006

Related U.S. Application Data

(60) Provisional application No. 60/628,763, filed on Nov. 16, 2004, provisional application No. 60/628,764, filed on Nov. 16, 2004.

(51) Int. Cl.
*G06K 9/00* (2006.01)
*A61B 6/00* (2006.01)

(52) U.S. Cl. .............. 382/128; 382/274; 378/6

(58) Field of Classification Search ......... 382/100, 382/103, 106, 108, 128–134, 162, 168, 180–181, 382/189, 255, 193–194, 260–261, 274, 276, 382/305, 312, 318, 147; 250/201.3, 458.1; 356/317, 310; 359/196; 378/6
See application file for complete search history.

(56) References Cited

U.S. PATENT DOCUMENTS

| | | |
|---|---|---|
| 3,614,193 A | 10/1971 | Beiser |
| 3,858,979 A | 1/1975 | Elbe |
| 3,880,497 A | 4/1975 | Bryngdahl |
| 3,891,302 A | 6/1975 | Dabby |
| 3,903,415 A | 9/1975 | Holzapfel |
| 3,916,182 A | 10/1975 | Dabby |
| 3,968,476 A | 7/1976 | McMahon |
| 4,011,435 A | 3/1977 | Phelps |
| 4,023,010 A | 5/1977 | Horst |
| 4,053,228 A | 10/1977 | Schiller |
| 4,053,433 A | 10/1977 | Lee |
| 4,131,337 A | 12/1978 | Moraw |
| 4,168,146 A | 9/1979 | Grubb |

(Continued)

FOREIGN PATENT DOCUMENTS

CH 598661 5/1978

(Continued)

OTHER PUBLICATIONS

"Compact Disc Arrayer"; V&P Scientific; Nov. 17, 2003; pp. 1-4.

(Continued)

*Primary Examiner*—Seyed Azarian
(74) *Attorney, Agent, or Firm*—Small Patent Law Group; Dean D. Small; Jason P. Gross

(57) ABSTRACT

The present invention features incorporating an adaptive spectral filter into a confocal scanner optical arrangement or other suitable optical device to permit real time control of the fluorescence signal spectrum being monitored. This new arrangement would allow for better balancing of the fluorescence signals in the analysis of the array.

18 Claims, 14 Drawing Sheets

U.S. PATENT DOCUMENTS

| | | |
|---|---|---|
| 4,301,139 A | 11/1981 | Feingers |
| 4,386,274 A | 5/1983 | Altshuler |
| 4,400,616 A | 8/1983 | Chevillat |
| 4,445,229 A | 4/1984 | Tasto |
| 4,447,546 A | 5/1984 | Hirschfeld |
| 4,537,504 A | 8/1985 | Baltes |
| 4,560,881 A | 12/1985 | Briggs |
| 4,562,157 A | 12/1985 | Lowe |
| 4,647,544 A | 3/1987 | Nicoli |
| 4,678,752 A | 7/1987 | Thorne |
| 4,685,480 A | 8/1987 | Eck |
| 4,688,240 A | 8/1987 | Hosemann et al. |
| 4,690,907 A | 9/1987 | Hibino |
| 4,701,754 A | 10/1987 | Provonchee |
| 4,716,121 A | 12/1987 | Block |
| 4,725,110 A | 2/1988 | Glenn |
| 4,740,468 A | 4/1988 | Weng |
| 4,740,688 A | 4/1988 | Edwards |
| 4,748,110 A | 5/1988 | Paul |
| 4,762,420 A | 8/1988 | Bowley |
| 4,767,719 A | 8/1988 | Finlan |
| 4,770,295 A | 9/1988 | Carveth |
| 4,807,950 A | 2/1989 | Glenn |
| 4,815,027 A | 3/1989 | Tokumitsu |
| 4,816,659 A | 3/1989 | Bianco |
| 4,822,746 A | 4/1989 | Walt |
| 4,841,140 A | 6/1989 | Sullivan |
| 4,877,747 A | 10/1989 | Stewart |
| 4,880,752 A | 11/1989 | Keck |
| 4,882,288 A | 11/1989 | North |
| 4,921,805 A | 5/1990 | Gebeyehu |
| 4,937,048 A | 6/1990 | Sakai |
| 4,958,376 A | 9/1990 | Leib |
| 4,992,385 A | 2/1991 | Godfrey |
| 5,002,867 A | 3/1991 | Macevicz |
| 5,003,600 A | 3/1991 | Deason |
| RE033,581 E | 4/1991 | Nicoli |
| 5,028,545 A | 7/1991 | Soini |
| 5,030,558 A | 7/1991 | Litman |
| 5,033,826 A | 7/1991 | Kolner |
| 5,065,008 A | 11/1991 | Hakamata |
| 5,067,155 A | 11/1991 | Bianco |
| 5,081,012 A | 1/1992 | Flanagan |
| 5,089,387 A | 2/1992 | Tsay |
| 5,090,807 A * | 2/1992 | Tai .............................. 356/310 |
| 5,091,636 A | 2/1992 | Takada |
| 5,095,194 A | 3/1992 | Barbanell |
| 5,100,238 A | 3/1992 | Nailor |
| 5,104,209 A | 4/1992 | Hill |
| 5,105,305 A | 4/1992 | Betzig |
| 5,114,864 A | 5/1992 | Walt |
| 5,115,121 A | 5/1992 | Bianco |
| 5,118,608 A | 6/1992 | Layton |
| 5,129,974 A | 7/1992 | Aurenius |
| 5,138,468 A | 8/1992 | Barbanell |
| 5,141,848 A | 8/1992 | Donovan |
| 5,143,853 A | 9/1992 | Walt |
| 5,144,461 A | 9/1992 | Horan |
| 5,160,701 A | 11/1992 | Brown, III |
| 5,166,813 A | 11/1992 | Metz |
| 5,192,980 A | 3/1993 | Dixon |
| 5,196,350 A | 3/1993 | Backman |
| 5,200,794 A | 4/1993 | Nishiguma |
| 5,218,594 A | 6/1993 | Tanno |
| 5,239,178 A | 8/1993 | Derndinger |
| 5,244,636 A | 9/1993 | Walt |
| 5,283,777 A | 2/1994 | Tanno |
| 5,291,006 A | 3/1994 | Nishiguma |
| 5,291,027 A | 3/1994 | Kita |
| 5,300,764 A | 4/1994 | Hoshino |
| 5,307,332 A | 4/1994 | Tinet |
| 5,310,686 A | 5/1994 | Sawyers |
| 5,329,352 A | 7/1994 | Jacobsen |
| 5,342,790 A | 8/1994 | Levine |
| 5,349,442 A | 9/1994 | Deason |
| 5,352,582 A | 10/1994 | Lichtenwalter |
| 5,364,797 A | 11/1994 | Olson |
| 5,367,588 A | 11/1994 | Hill |
| 5,372,783 A | 12/1994 | Lackie |
| 5,374,816 A | 12/1994 | Bianco |
| 5,374,818 A | 12/1994 | Bianco |
| 5,388,173 A | 2/1995 | Glenn |
| 5,394,234 A | 2/1995 | Bianco |
| 5,395,558 A | 3/1995 | Tsai |
| 5,426,297 A | 6/1995 | Dunphy |
| 5,432,329 A | 7/1995 | Colgate |
| 5,442,433 A | 8/1995 | Hoshino |
| 5,448,659 A | 9/1995 | Tsutsui |
| 5,451,528 A | 9/1995 | Raymoure |
| 5,455,178 A | 10/1995 | Fattinger |
| 5,461,475 A | 10/1995 | Lerner |
| 5,465,176 A | 11/1995 | Bianco |
| 5,468,649 A | 11/1995 | Shah |
| 5,506,674 A | 4/1996 | Inoue |
| 5,514,785 A | 5/1996 | Van Ness |
| 5,528,045 A | 6/1996 | Hoffman |
| 5,547,849 A | 8/1996 | Baer |
| 5,559,613 A | 9/1996 | Deveaud-Pledran |
| 5,585,639 A | 12/1996 | Dorsel |
| 5,587,832 A | 12/1996 | Krause |
| 5,607,188 A | 3/1997 | Bahns |
| 5,610,287 A | 3/1997 | Nikiforov |
| 5,620,853 A | 4/1997 | Smethers |
| 5,621,515 A | 4/1997 | Hoshino |
| 5,624,850 A | 4/1997 | Kumar |
| 5,625,472 A | 4/1997 | Mizrahi |
| 5,627,040 A | 5/1997 | Bierre |
| 5,627,663 A | 5/1997 | Horan |
| 5,633,724 A | 5/1997 | King |
| 5,633,790 A | 5/1997 | Gritter |
| 5,633,975 A * | 5/1997 | Gary et al. .................. 385/147 |
| 5,663,790 A | 9/1997 | Ekstrom |
| 5,667,976 A | 9/1997 | Van Ness |
| 5,671,308 A | 9/1997 | Inoue |
| 5,682,244 A | 10/1997 | Barlow |
| 5,712,912 A | 1/1998 | Tomko |
| 5,721,435 A | 2/1998 | Troll |
| 5,729,365 A | 3/1998 | Sweatt |
| 5,736,330 A | 4/1998 | Fulton |
| 5,742,432 A | 4/1998 | Bianco |
| 5,745,615 A | 4/1998 | Atkins |
| 5,745,617 A | 4/1998 | Starodubov |
| 5,759,778 A | 6/1998 | Li |
| 5,760,961 A | 6/1998 | Tompkin |
| 5,766,956 A | 6/1998 | Groger |
| 5,771,251 A | 6/1998 | Kringlebotn |
| 5,776,694 A | 7/1998 | Sheiness |
| 5,793,502 A | 8/1998 | Bianco |
| 5,798,273 A | 8/1998 | Shuler |
| 5,799,231 A | 8/1998 | Gates |
| 5,801,857 A | 9/1998 | Heckenkamp |
| 5,804,384 A | 9/1998 | Muller |
| 5,812,272 A | 9/1998 | King |
| 5,822,472 A | 10/1998 | Danielzik |
| 5,824,478 A | 10/1998 | Muller |
| 5,824,557 A | 10/1998 | Burker |
| 5,830,622 A | 11/1998 | Canning |
| 5,831,698 A | 11/1998 | Depp |
| 5,837,475 A | 11/1998 | Dorsel |
| 5,837,552 A | 11/1998 | Cotton |
| 5,841,555 A | 11/1998 | Bianco |
| 5,846,737 A | 12/1998 | Kang |
| 5,874,187 A | 2/1999 | Colvin |
| 5,881,197 A | 3/1999 | Dong |

| | | |
|---|---|---|
| 5,895,750 A | 4/1999 | Mushahwar |
| 5,922,550 A | 7/1999 | Everhart |
| 5,922,617 A | 7/1999 | Wang |
| 5,925,562 A | 7/1999 | Nova |
| 5,925,878 A | 7/1999 | Challener |
| 5,945,679 A | 8/1999 | Dorsel |
| 5,972,542 A | 10/1999 | Starodubov |
| 5,976,896 A | 11/1999 | Kumar |
| 5,981,166 A | 11/1999 | Mandecki |
| 5,986,838 A | 11/1999 | Thomas, III |
| 5,989,923 A | 11/1999 | Lowe |
| 5,992,742 A | 11/1999 | Sullivan |
| 5,998,796 A | 12/1999 | Liu |
| 6,001,510 A | 12/1999 | Meng |
| 6,005,691 A | 12/1999 | Grot |
| 6,017,754 A | 1/2000 | Chesnut |
| 6,025,129 A | 2/2000 | Nova |
| 6,025,283 A | 2/2000 | Robers |
| 6,027,694 A | 2/2000 | Boulton |
| 6,030,581 A | 2/2000 | Virtanen |
| 6,035,082 A | 3/2000 | Murphy |
| 6,036,807 A | 3/2000 | Brongers |
| 6,043,880 A | 3/2000 | Andrews |
| 6,046,925 A | 4/2000 | Tsien |
| 6,049,727 A | 4/2000 | Crothall |
| 6,057,107 A | 5/2000 | Fulton |
| 6,060,256 A | 5/2000 | Everhart |
| 6,067,167 A | 5/2000 | Atkinson |
| 6,067,392 A | 5/2000 | Wakami |
| 6,078,048 A | 6/2000 | Stevens |
| 6,084,995 A | 7/2000 | Clements |
| 6,087,186 A | 7/2000 | Cargill |
| 6,096,496 A | 8/2000 | Frankel |
| 6,096,596 A | 8/2000 | Gonzalez |
| 6,097,485 A | 8/2000 | Lievan |
| 6,103,535 A | 8/2000 | Pilevar |
| 6,118,127 A | 9/2000 | Liu |
| 6,128,077 A | 10/2000 | Jovin et al. |
| 6,137,931 A | 10/2000 | Ishikawa |
| 6,143,247 A | 11/2000 | Sheppard, Jr. |
| 6,156,501 A | 12/2000 | McGall |
| 6,159,748 A | 12/2000 | Hechinger |
| 6,160,240 A | 12/2000 | Momma |
| 6,160,656 A | 12/2000 | Mossberg |
| 6,164,548 A | 12/2000 | Curiel |
| 6,165,592 A | 12/2000 | Berger |
| 6,165,648 A | 12/2000 | Covin |
| 6,174,648 B1 | 1/2001 | Terao |
| 6,194,563 B1 | 2/2001 | Cruickshank |
| 6,204,969 B1 | 3/2001 | Jang |
| 6,214,560 B1 | 4/2001 | Yguerabide |
| 6,218,194 B1 | 4/2001 | Lyndin |
| 6,221,579 B1 | 4/2001 | Everhart |
| 6,229,635 B1 | 5/2001 | Wulf |
| 6,229,827 B1 | 5/2001 | Fernald |
| 6,229,941 B1 | 5/2001 | Yoon |
| 6,242,056 B1 | 6/2001 | Spencer |
| 6,259,450 B1 | 7/2001 | Chiabrera |
| 6,268,128 B1 | 7/2001 | Collins |
| 6,277,628 B1 | 8/2001 | Johann |
| 6,284,459 B1 | 9/2001 | Nova |
| 6,285,806 B1 | 9/2001 | Kersey |
| 6,288,220 B1 | 9/2001 | Kambara |
| 6,292,282 B1 | 9/2001 | Mossberg |
| 6,292,319 B1 | 9/2001 | Thomas, III |
| 6,301,047 B1 | 10/2001 | Hoshino |
| 6,304,263 B1 | 10/2001 | Chiabrera |
| 6,306,587 B1 | 10/2001 | Royer |
| 6,309,601 B1 | 10/2001 | Juncosa |
| 6,312,961 B1 | 11/2001 | Voirin |
| 6,313,771 B1 | 11/2001 | Munroe |
| 6,314,220 B1 | 11/2001 | Mossberg |
| 6,319,668 B1 | 11/2001 | Nova |
| 6,321,007 B1 | 11/2001 | Sanders |
| 6,322,932 B1 | 11/2001 | Covin |
| RE037,473 E | 12/2001 | Challener |
| 6,329,963 B1 | 12/2001 | Chiabrera |
| 6,331,273 B1 | 12/2001 | Nova |
| 6,340,588 B1 | 1/2002 | Nova |
| 6,352,854 B1 | 3/2002 | Nova |
| 6,355,198 B1 | 3/2002 | Kim |
| 6,355,432 B1 | 3/2002 | Fodor |
| 6,356,681 B1 | 3/2002 | Chen |
| 6,359,734 B1 | 3/2002 | Staub |
| 6,361,958 B1 | 3/2002 | Shieh |
| 6,363,097 B1 | 3/2002 | Linke |
| 6,371,370 B2 | 4/2002 | Sadler |
| 6,372,428 B1 | 4/2002 | Nova |
| 6,383,754 B1 | 5/2002 | Kaufman |
| 6,391,562 B2 | 5/2002 | Kambara |
| 6,395,558 B1 | 5/2002 | Duveneck |
| 6,399,295 B1 | 6/2002 | Kaylor |
| 6,399,935 B1 | 6/2002 | Jovin et al. |
| 6,403,320 B1 | 6/2002 | Read |
| 6,406,841 B1 | 6/2002 | Lee |
| 6,406,848 B1 | 6/2002 | Bridgham |
| 6,416,714 B1 | 7/2002 | Nova |
| 6,416,952 B1 | 7/2002 | Pirrung |
| 6,417,010 B1 | 7/2002 | Cargill |
| 6,428,707 B1 | 8/2002 | Berg |
| 6,428,957 B1 | 8/2002 | Delenstarr |
| 6,429,022 B1 | 8/2002 | Kunz |
| 6,433,849 B1 | 8/2002 | Lowe |
| 6,436,651 B1 | 8/2002 | Everhart |
| 6,440,667 B1 | 8/2002 | Fodor |
| 6,456,762 B1 | 9/2002 | Nishiki |
| RE037,891 E | 10/2002 | Collins |
| 6,462,770 B1 | 10/2002 | Cline et al. |
| 6,489,606 B1 | 12/2002 | Kersey |
| 6,496,287 B1 | 12/2002 | Seiberle |
| 6,506,342 B1 | 1/2003 | Frankel |
| 6,514,767 B1 | 2/2003 | Natan |
| 6,515,753 B2 | 2/2003 | Maher |
| 6,522,406 B1 | 2/2003 | Rovira |
| 6,524,793 B1 | 2/2003 | Chandler |
| 6,533,183 B2 | 3/2003 | Aasmul |
| 6,542,673 B1 | 4/2003 | Holter |
| 6,544,739 B1 | 4/2003 | Fodor |
| 6,545,758 B1 * | 4/2003 | Sandstrom ................. 356/317 |
| 6,560,017 B1 | 5/2003 | Bianco |
| 6,565,770 B1 | 5/2003 | Mayer |
| 6,576,424 B2 | 6/2003 | Fodor |
| 6,578,712 B2 | 6/2003 | Lawandy |
| 6,592,036 B2 | 7/2003 | Sadler |
| 6,594,421 B1 | 7/2003 | Johnson |
| 6,609,728 B1 | 8/2003 | Voermann |
| 6,613,581 B1 | 9/2003 | Wada |
| 6,618,342 B1 | 9/2003 | Johnson |
| 6,622,916 B1 | 9/2003 | Bianco |
| 6,628,439 B2 | 9/2003 | Shiozawa |
| 6,632,655 B1 | 10/2003 | Mehta |
| 6,635,470 B1 | 10/2003 | Vann |
| 6,635,863 B1 | 10/2003 | Nihommori |
| 6,646,243 B2 | 11/2003 | Pirrung |
| 6,657,758 B1 * | 12/2003 | Garner ................. 359/196 |
| 6,660,147 B1 | 12/2003 | Woudenberg |
| 6,678,429 B2 | 1/2004 | Mossberg |
| RE038,430 E | 2/2004 | Rosenstein |
| 6,689,316 B1 | 2/2004 | Blyth |
| 6,692,031 B2 | 2/2004 | McGrew |
| 6,692,912 B1 | 2/2004 | Boles |
| 6,794,658 B2 * | 9/2004 | MacAulay et al. ....... 250/458.1 |
| 6,806,954 B2 * | 10/2004 | Sandstrom ................. 356/317 |
| 6,982,996 B1 | 1/2005 | Putnam |
| 6,858,184 B2 | 2/2005 | Pelrine |
| 6,874,639 B2 | 4/2005 | Lawandy |

| | | | | | | |
|---|---|---|---|---|---|---|
| 6,881,789 B2 | 4/2005 | Bossé | | 2007/0121181 A1 | 5/2007 | Moon |
| 6,892,001 B2 | 5/2005 | Ohta | | 2008/0170664 A1 | 7/2008 | Kalman |
| 6,905,885 B2 | 6/2005 | Colston | | | | |
| 6,908,737 B2 | 6/2005 | Ravkin | | FOREIGN PATENT DOCUMENTS | | |
| 6,919,009 B2 | 7/2005 | Stonas et al. | | DE | 2416652 | 10/1975 |
| 7,045,049 B1 | 5/2006 | Natan et al. | | EP | 0 395 300 | 10/1990 |
| 7,092,160 B2 | 8/2006 | Putnam | | EP | 0 723 149 | 7/1996 |
| 7,106,513 B2 | 9/2006 | Moon | | EP | 0 798 573 A1 | 10/1997 |
| 7,126,755 B2 | 10/2006 | Moon | | EP | 0 911 667 A1 | 4/1999 |
| 7,225,082 B1 | 5/2007 | Natan | | EP | 0 916 981 A1 | 5/1999 |
| 7,339,148 B2 * | 3/2008 | Kawano et al. .......... 250/201.3 | | EP | 916981 | 5/1999 |
| 2001/0007775 A1 | 7/2001 | Seul | | EP | 0 972 817 A1 | 1/2000 |
| 2002/0000471 A1 | 1/2002 | Aasmul | | EP | 1182054 | 2/2002 |
| 2002/0006664 A1 | 1/2002 | Sabatini | | EP | 1219979 | 7/2002 |
| 2002/0018430 A1 | 2/2002 | Heckenkamp | | GB | 2 118 189 | 10/1983 |
| 2002/0021003 A1 | 2/2002 | McGrew | | GB | 2129551 | 5/1984 |
| 2002/0022273 A1 | 2/2002 | Empedocles | | GB | 2 138 821 | 10/1984 |
| 2002/0025534 A1 | 2/2002 | Goh | | GB | 2 299 235 | 9/1996 |
| 2002/0031783 A1 | 3/2002 | Empedocles | | GB | 2 306 484 | 5/1997 |
| 2002/0034747 A1 | 3/2002 | Bruchez | | GB | 2 319 838 | 6/1998 |
| 2002/0039732 A1 | 4/2002 | Bruchez | | GB | 2372100 | 8/2002 |
| 2002/0074513 A1 | 6/2002 | Abel | | JP | 58143254 | 8/1983 |
| 2002/0084329 A1 | 7/2002 | Kaye | | JP | 08102544 | 4/1986 |
| 2002/0090650 A1 | 7/2002 | Empedocles | | JP | 01047950 | 2/1989 |
| 2002/0094528 A1 | 7/2002 | Salafsky | | JP | 200300467 | 12/1990 |
| 2002/0097658 A1 | 7/2002 | Worthington | | JP | 10160705 | 6/1998 |
| 2002/0155490 A1 | 10/2002 | Skinner | | JP | 11119029 | 4/1999 |
| 2002/0174918 A1 | 11/2002 | Fujimura | | JP | 20035521 | 2/2000 |
| 2002/0197456 A1 | 12/2002 | Pope | | JP | 00249706 | 9/2000 |
| 2003/0008323 A1 | 1/2003 | Ravkin | | WO | WO 91/06496 | 5/1991 |
| 2003/0021003 A1 | 1/2003 | Ono | | WO | WO 93/09668 | 5/1993 |
| 2003/0032203 A1 | 2/2003 | Sabatini | | WO | WO 94/28119 | 12/1994 |
| 2003/0077038 A1 | 4/2003 | Murashima | | WO | WO 96/24061 | 8/1996 |
| 2003/0082568 A1 | 5/2003 | Phan | | WO | WO 96/36436 | 11/1996 |
| 2003/0082587 A1 | 5/2003 | Seul | | WO | WO9636436 | 11/1996 |
| 2003/0129654 A1 | 7/2003 | Ravkin | | WO | WO 97/12680 | 4/1997 |
| 2003/0138208 A1 | 7/2003 | Pawlak | | WO | WO 97/15690 | 5/1997 |
| 2003/0142704 A1 | 7/2003 | Lawandy | | WO | WO 97/17258 | 5/1997 |
| 2003/0142713 A1 | 7/2003 | Lawandy | | WO | WO 97/31282 | 8/1997 |
| 2003/0153006 A1 | 8/2003 | Washizu | | WO | WO 97/34171 | 9/1997 |
| 2003/0162296 A1 | 8/2003 | Lawandy | | WO | WO 98/04740 | 2/1998 |
| 2003/0184703 A1 | 10/2003 | Greene et al. | | WO | WO 98/24549 | 6/1998 |
| 2003/0203390 A1 | 10/2003 | Kaye | | WO | WO 99/02266 | 1/1999 |
| 2003/0228610 A1 | 12/2003 | Seul | | WO | WO 99/09042 | 2/1999 |
| 2004/0047030 A1 | 3/2004 | MacAulay | | WO | WO 99/32654 | 7/1999 |
| 2004/0075907 A1 | 4/2004 | Moon | | WO | WO 99/42209 | 8/1999 |
| 2004/0100636 A1 | 5/2004 | Somekh et al. | | WO | 00/08443 | 2/2000 |
| 2004/0125370 A1 | 7/2004 | Montagu | | WO | WO 00/08443 | 2/2000 |
| 2004/0125424 A1 | 7/2004 | Moon | | WO | WO0016893 | 3/2000 |
| 2004/0126875 A1 | 7/2004 | Putnam | | WO | WO 00/37914 | 6/2000 |
| 2004/0132205 A1 | 7/2004 | Moon | | WO | WO 00/37969 | 6/2000 |
| 2004/0156471 A1 | 8/2004 | Sakata | | WO | WO 00/39617 | 7/2000 |
| 2004/0170356 A1 | 9/2004 | Iazikov | | WO | WO0061198 | 10/2000 |
| 2004/0175842 A1 | 9/2004 | Roitman | | WO | WO0158583 | 8/2001 |
| 2004/0209376 A1 | 10/2004 | Natan | | WO | WO0171322 | 9/2001 |
| 2004/0233485 A1 | 11/2004 | Moon | | WO | WO 01/78889 | 10/2001 |
| 2004/0263923 A1 | 12/2004 | Moon | | WO | WO0178889 | 10/2001 |
| 2005/0042764 A1 | 2/2005 | Sailor | | WO | WO 02/059603 | 8/2002 |
| 2005/0220408 A1 | 10/2005 | Putnam | | WO | WO02059306 | 8/2002 |
| 2005/0227252 A1 | 10/2005 | Moon | | WO | WO02064829 | 8/2002 |
| 2005/0270603 A1 | 12/2005 | Putnam | | WO | WO03061983 | 7/2003 |
| 2006/0023310 A1 | 2/2006 | Putnam | | WO | WO03091731 | 11/2003 |
| 2006/0028727 A1 | 2/2006 | Moon | | WO | WO2004011940 | 2/2004 |
| 2006/0057729 A1 | 3/2006 | Moon | | WO | WO2004015418 | 2/2004 |
| 2006/0063271 A1 | 3/2006 | Putnam | | WO | WO 2004/019276 | 3/2004 |
| 2006/0071075 A1 | 4/2006 | Moon et al. | | WO | WO 2004/025561 | 3/2004 |
| 2006/0072177 A1 | 4/2006 | Putnam | | WO | WO 2004/025563 | 3/2004 |
| 2006/0118630 A1 | 6/2006 | Kersey | | WO | WO2004019276 | 3/2004 |
| 2006/0119913 A1 | 6/2006 | Moon | | WO | WO2004024328 | 3/2004 |
| 2006/0132877 A1 | 6/2006 | Kersey | | WO | WO2004025562 | 3/2004 |
| 2006/0134324 A1 | 6/2006 | Putnam | | WO | WO2004046697 | 6/2004 |
| 2006/0139635 A1 | 6/2006 | Kersey | | WO | WO2004066210 | 8/2004 |
| 2006/0160208 A1 | 7/2006 | Putnam | | | | |

| | | |
|---|---|---|
| WO | WO 2005/026729 | 3/2005 |
| WO | WO 2005/027031 | 3/2005 |
| WO | WO 2005/029047 | 3/2005 |
| WO | WO 2005/033681 | 4/2005 |
| WO | WO 2005/050207 | 6/2005 |
| WO | WO 2005/079544 | 9/2005 |
| WO | WO 2006/020363 | 2/2006 |
| WO | WO 2006/055735 | 5/2006 |
| WO | WO 2006/055736 | 5/2006 |
| WO | WO 2006/076053 | 7/2006 |

OTHER PUBLICATIONS

"Electronically Scanned Confocal Imaging System"; IBM Technical Disclosure Bulletin; vol. 36; No. 06B; Jun. 1993; pp. 261-262.
"Ben Beune Patent Licensing Director of Philips IP&S"; Replication & Duplication-News & Technology; Jan.-Feb. 2002; pp. 1-2.
Andrew Marshall; "DNA Chips: Array of Possibilities"; Nature Biotechnology vol. 16 Jan. 1998; pp. 27-31.
Burstein Technology, Inc.; "Angel Strategies Tombstone"; 1 pg. (2006).
de Beer et al., "Forward-Scattering Degenerate Four-Wave Mixing for Sensitive Absorption Detection in Microseparation Systems Coupling to Micro-Column Liquid Chromatography"; Journal of Chromatography A. 811 (1998); pp. 35-45.
Fonjallaz et al., "Interferometric Side Diffraction Technique for the Characterisation of Fiber Gratings"; 1999 OSA Conference, Sep. 23-25; 3 pgs.
G. Kakarantzas et al.; "Transmission Filters Based on periodically Micro-tapered Fibre"; CLE0/2000/Friday Morning; 8:45 a.m.; pp. 574-575 (2000).
Hideki Kambara; Recent Progress In fluorescent DNA Analyzers and Methods; Current Topics in Analytical checmistry; vol. 1, (1998) pp. 21-36.
Ivan Oransky; "Sequencing on Compact Disc? Microgenomics of Breast Cancer; Better Binding Site Prediction"; vol. 17 / Issue 13 / 35 / Jun. 30, 2003; 13 pgs.
Kashyap R.; "Fiber Bragg Gratings"; Academic Press, Ch. 9; pp. 430-433 (1995).
Kogelnik H; "Coupled Wave Theory for Thick Hologram Gratings"; The Bell System Technical Journal, 48(9):2909-2947 (1969).
Krug P., "Measurement of Index Modulation Along an Optical Fiber Bragg Grating"; Optics Letters, 20(17):1767-1769.
Leith et al., "Holographic Data Storage in Three-Dimensional Media"; Applied Optics, vol. 5, No. 8, Aug. 1966; 21 pgs.
Mark O. Worthington; "Curriculum Vitae"; Jan. 5, 2004; 4 pgs.
Masato Mitsuhashi; "Gene Manipulation on Plastic Plates"; Nature, vol. 357, Jun. 11, 1992; pp. 519-520.
Michael C. Needels et al.; "Generation and Screening of an Oligonucleotide-Encoded Synthetic Peptide Library"; Proc Natl. Acad. Sci. USA, vol. 90;pp. 10700-10704, Nov. 1993.
Michael J. Kozal; "Extensive Polymorphisms Observed in HIV-1 Clade B Protease Gene Using High-Density Oligonucleotide Arrays"; Nature Medicine, vol. 2, No. 7, Jul. 1996; pp. 753-759.
Shelia R. Nicerwarner-Peña, "Submicrometer Metallic Barcodes"; Science, vol. 294; Oct. 5, 2001; 5 pgs.
Thomas Laurell; "Enhanced Enzyme Activity in Silicon Integrated Enzyme Reactors Utilizing Porous Silicon as the Coupling Matrix"; Sensor & Actuators B 31(1996); pp. 161-166.
Vander Lugt; "Design Relationships For Holographic Memories"; Applied Optics, vol. 12, No. 7, Jul. 1973; pp. 1675-1685.

W.R. Rigby; "An Anodizing Process for the Production of Inorganic Microfiltration Membranes"; 2436Transactions of the Institute of Metal Finishing;68Aug. 1990,Part 3 p. 95-98.
Yoshinobu Kohara; "DNA Probes on Beads Arrayed in a Capillary, 'Bead-Array',Exhibited High Hybridization Performance"; Nucleic Acids Research, 2002, vol. 30, No. 16 e87; 7 pgs.
Introduction to Flow Cytometry: A Learning Guide, BD Biosciences, San Jose, CA, Apr. 2000, 54 pgs.
Jain KK, Nanodiagnostics: Application of Nanotechnology in Molecular Diagnostics, Expert Review of Molecular Diagnostics 3(2):153-161 (2003), XP008038849.
Lide (CRC Handbook of Chemistry and Physics, 71st ed.), 1991.
Othonos, X. Lee; Superimposed Multiple Bragg Gratings, Nov. 10, 1994, vol. 30, No. 23.
Patil et al. (AAPS PharmSciTech, Mar. 24, 2006, vol. 7, pp. E1-E7).
Po Ki Yuen, Microbarcode Sorting Device; Science & Technology, Corning Incorparated, Corning, New York 14831-0007, USA, 2003.
International Search Report and Written Opinion for International Application No. PCT/US2003/26315.
International Search Report and Written Opinion for International Application No. PCT/US2003/26316.
International Search Report for International Application No. PCT/US2003/28862.
International Search Report for International Application No. PCT/US2003/28874.
International Search Report for International Application No. PCT/US2003/28875.
International Search Report for International Application No. PCT/US2003/28887.
International Search Report for International Application No. PCT/US2003/28890.
International Search Report and Written Opinion for International Application No. PCT/US2003/29164.
International Search Report for International Application No. PCT/US2003/29244.
International Search Report and Written Opinion for International Application No. PCT/US2004/01685.
International Search Report and Written Opinion for International Application No. PCT/US2004/30037.
International Search Report and Written Opinion for International Application No. PCT/US2004/30038.
International Search Report and Written Opinion for International Application No. PCT/US2004/30300.
International Search Report and Written Opinion for International Application No. PCT/US2004/32084.
International Search Report and Written Opinion for International Application No. PCT/US2004/38416.
International Search Report and Written Opinion for International Application No. PCT/US2005/05743.
International Search Report and Written Opinion for International Application No. PCT/US2005/05745.
International Search Report and Written Opinion for International Application No. PCT/US2005/26289.
International Search Report and Written Opinion for International Application No. PCT/US2005/33694.
International Search Report and Written Opinion for International Application No. PCT/US2005/41730.
International Search Report and Written Opinion for International Application No. PCT/US2005/41731.
US 6,780,301, 08/2004, Natan (withdrawn)

* cited by examiner

ILLUSTRATION OF MICROARRAY SHOWING THE BASIC PROBLEM IN THE ART

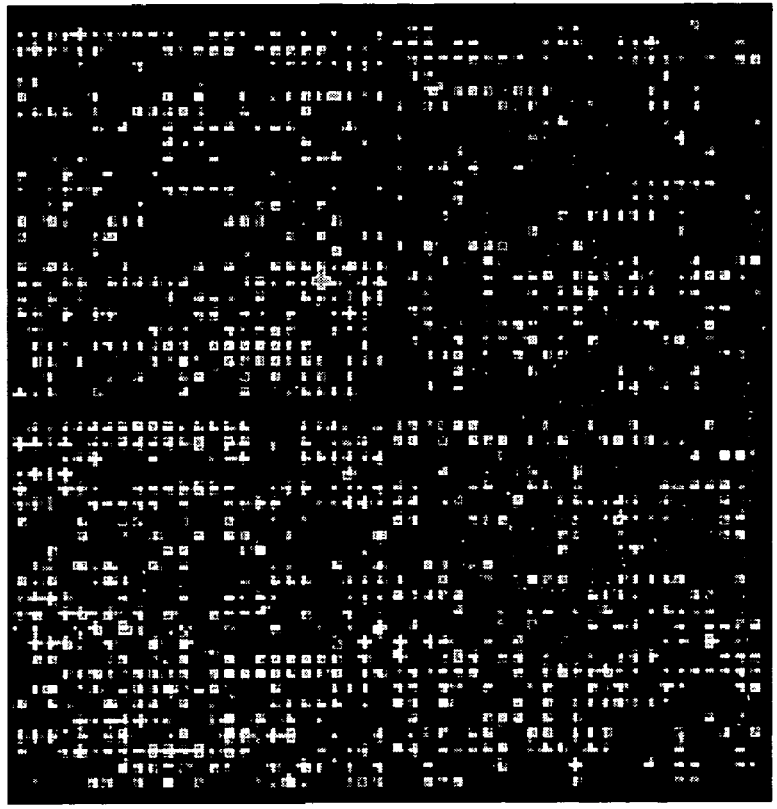

FIG. 1A

- FLUORESCENCE SIGNALS VARY STRONGLY ACROSS A BIOCHIP OR MICROARRAY, E.G. SPOTTED ARRAY DUE TO:
  - DIFFERENT DEGREES OF HYBRIDIZATION
  - DIFFERENT FLUORESCENCE EFFICIENCY

- DIFFERENT ARRAYS/TESTS MAY REQUIRE DIFFERENT FLUORESCENCE MARKERS; 2 IS TYPICAL, BUT OFTEN MORE ARE USED.

- BULK-OPTIC FILTERS AND FILTER WHEELS OFTEN USED TO ALLOW DETECTION OF DIFFERENT FLUORESCENCE SPECTRA, BUT ARE NOT FLEXIBLE AND READILY SCALABLE.

ILLUSTRATION OF MICROARRAY SHOWING THE BASIC PROBLEM IN THE ART

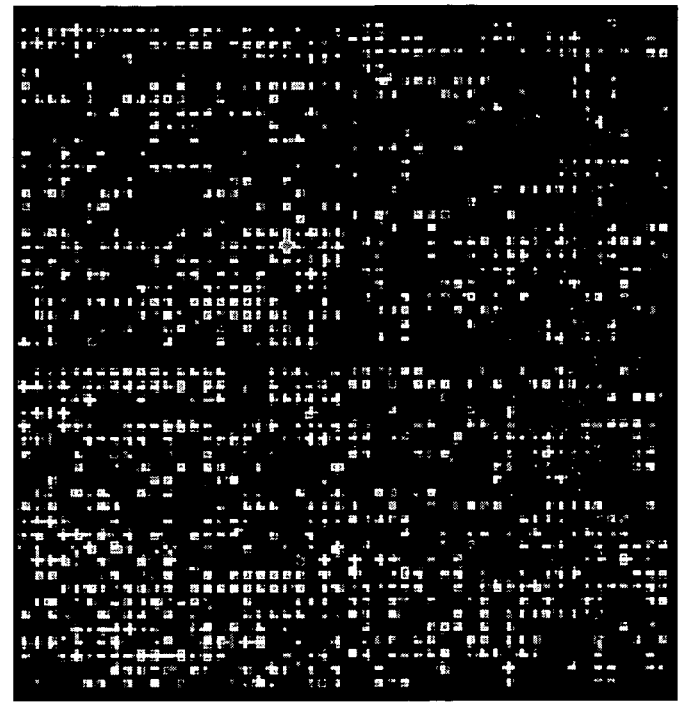

- FLUORESCENCE SIGNALS VARY STRONGLY ACROSS A BIOCHIP OR MICROARRAY (E.G. SPOTTED ARRAY) DUE TO DIFFERENT DEGREES OF HYBRIDIZATION

- WIDE DYNAMIC RANGE IN DETECTION SYSTEM IS REQUIRED TO MEASURE ALL THE EXPERSION ACTIVITY

- DMD ACTS AS A SPATIAL LIGHT MODULATOR TO ATTENUATE THE STRONGER SIGNALS, THUS PROVIDING MORE ABILITY TO MEASURE WEAK SIGNALS

- EQUALIZATION EFFECT "CLAMPS", OR "LIMITS" THE POWER AT A THRESHOLD LEVEL (E.G. ONCE THE SIGNAL RISES ABOVE A PARTICULAR VALUE, THE DMD MIRRORS ASSOCIATED WITH THE SPATIAL LOCATION ARE ACTIVATED TO INDUCE AN ATTENUATION)

- DETECTOR SYSTEM CAN EFFECTIVELY PROVIDE A WIDER DYNAMIC RANGE

- CURRENT SYSTEMS ATTAIN 3+ DECADES, THIS MAY IMPROVE THINGS TO 4+ TO 5 DECADES

*FIG. 1B*

SCANNER HAVING SPATIAL LIGHT MODULATOR

CROSS-REFERENCE TO RELATED CASES

This application claims benefit to provisional patent application no. 60/628,763 (WFVA/CyVERA nos. 714-1.16/CV 0031PR), filed Nov. 16, 2004, as well as provisional patent application no. 60/628,764 (WFVA/CyVERA nos. 714-1.17/CV 0030PR), filed Nov. 16, 2004, which are both hereby incorporated by reference in their entirety.

BACKGROUND OF THE INVENTION

1. Technical Field

The present invention relates to an optical scanner; and more particularly, an optical scanner for fluorescence monitoring of an optical device, such as a microarray or biochip (spotted array or other biochip format), or other suitable optical device.

2. Description of Related Art

A common class of experiments, known as a multiplexed assay or multiplexed experiment, comprises mixing (or reacting) a labeled target analyte or sample (which may have known or unknown properties or sequences) with a set of "probe" or reference substances (which also may have known or unknown properties or sequences). Multiplexing allows many properties of the target analyte to be probed or evaluated simultaneously (i.e., in parallel). For example, in a gene expression assay, the "target" analyte, usually an unknown sequence of DNA, is labeled with a fluorescent molecule to form the labeled analyte.

In a known DNA/genomic sequencing assay, each probe consists of known DNA sequences of a predetermined length, which are attached to a labeled (or encoded) bead or to a known location on a substrate.

When the labeled target analyte is mixed with the probes, segments of the DNA sequence of the labeled target analyte will selectively bind to complementary segments of the DNA sequence of the known probe. The known probes are then spatially separated and examined for fluorescence. The beads that fluoresce indicate that the DNA sequence strands of the target analyte have attached or hybridized to the complementary DNA on that bead. The DNA sequences in the target analyte can then be determined by knowing the complementary DNA (or cDNA) sequence of each known probe to which the labeled target is attached. In addition the level of fluorescence is indicative of how many of the target molecules hybridized to the probe molecules for a given bead.

Generally, the probes are either spatially separated or otherwise labeled to identify the probe, and ultimately the "target" analyte. One approach separates the probes in a predetermined grid, where the probe's identity is linked to its position on the grid. One example of this is a "chip" format, where DNA is attached to a 2-D substrate, biochip or microarray, where oligomer DNA sequences are selectively attached (either by spotting or grown) onto small sections or spots on the surface of the substrate in a predetermined spatial order and location on a substrate (usually a planar substrate, such as a glass microscope slide).

However, in the prior art it is known that fluorescence signals vary strongly across the biochip or microarray, e.g. spotted array, due to:

Different degrees of hybridization; and

Different fluorescence efficiency.

The reader is referred to FIG. 1A, which shows the basic problem in the art related to the variation of the fluorescence signals across a micromirror. Moreover, different arrays/tests may require different fluorescence markers; two is typical, but often more are used; and bulk-optic filters and filter wheels are often used to allow detection of different fluorescence spectra, but these devices are not flexible and readily scalable.

Moreover, in the prior art it is also known that fluorescence signals vary strongly across a biochip or microarray (e.g. spotted array) due to different degrees of hybridization. See FIG. 1B, which sets forth another basic problem in the art related to the variation of the fluorescence signals across a micromirror. A wide dynamic range in the known detection system is required to measure all the expersion activity.

In view of this, there is a need in the art for an optical scanner to overcome the shortcomings of the known prior art scanners.

SUMMARY OF THE INVENTION

In imaging biochips/microarrays confocal scanners/readers are commonly used. Confocal optics provide excellent suppression of 'out-of-focal-plane' light rejection, and high lateral resolution. The image is often recorded using multiple fluorescence tags that indicate the degree of binding or hybridization of target biomolecules to probes immobilized on the biochip/microarray.

The present invention features incorporating an adaptive spectral filter into a confocal scanner optical arrangement or other suitable optical device to permit real time control of the fluorescence signal spectrum being monitored. This new arrangement would allow for better balancing of the fluorescence signals in the analysis of the array.

Advantages of the present invention include the following:

The adaptive filter provides for fluorescence monitoring of microarray and biochips replacing filter wheels and fixed filters.

The solution is readily scalable to different fluorescent targets and the filter can be configured to "spectrally match" the fluorescence target spectrum.

The use of a DLP (or other a SLM) provides the ability to provide 'gain-control' of the optical fluorescence signals.

The use of the DLP as a spatial light modulator provides a good fill factor (i.e. relatively low insertion loss) and high contrast ratio (>300), thus, in principle, provides a good rejection of out-of-band noise and stray signals.

Other advantages include the following:

A frequency modulated approach provides for the simultaneous detection of multiple fluorescence targets.

Each fluorescent signal is modulated at a different rate (via modulation of the associated DMD mirrors at that rate).

May enable faster scanning of arrays.

Moreover, in imaging biochips/microarrays on CCDs, dynamic range is of course important, particularly regarding sensitivity in expression analysis etc.

According to the present invention, the adaptive spectral filter also equalizes intensities of the fluorescence signal spectrum across a predetermined portion of the surface of the spatial light modulator. In particular, a DLP is arranged between the array plane and image plane to add a 2D "gain control" element. After the first 'image' is captured, the DLP could be adjusted (in a PCM video-like format as one option) to add attenuation to various spatial regions, e.g., a 2D dynamic gain equalization (DGE).

This technique would allow for better balancing of the fluorescence signals and reduce blooming and crosstalk.

In effect, the DMD acts as a spatial light modulator to attenuate the stronger signals, thus providing more ability to measure weak signals.

The equalization effect "clamps", or "limits" the power at a threshold level (e.g. once the signal rises above a particular value, the DMD mirrors associated with the spatial location are activated to induce an attenuation).

According to the present invention, the detector system can effectively provide a wider dynamic range of operation.

Current systems attain 3+ decades, the present invention is likely to improve performance to 4+ to 5 decades.

Advantages of this aspect of the present invention include the following:

The effective dynamic range of an imaging system is extended by applying known attenuation levels in a spatially varying manner determined by the 'brightness' of local microarray spots/elements.

This serves as a "limiter" for the spot intensity coupled to the image detector, thus allowing weaker signals to be more effectively monitored in the presence of strong adjacent signals.

The use of the DLP as a spatial light modulator provides a good fill factor and high contrast ratio (>100), thus in principle provides an extension to the detection dynamic range of two orders of magnitude.

BRIEF DESCRIPTION OF THE DRAWING

The drawing, which are not drawn to scale, includes the following Figures

FIG. 1A shows a diagram of fluorescence signals that vary strongly across a biochip or microarray, which is a problem in the art that the present invention seeks to solve.

FIG. 1B shows a diagram of fluorescence signals that vary strongly across a biochip or microarray, which is a problem in the art that the present invention seeks to solve.

FIG. 5 includes FIGS. 5(a) and (b) for fluorescence signals sequentially read, wherein FIG. 5(a) shows a DMD having mirrors set to sequentially provide a fluorescence filter for each target, F1, F2, and wherein

FIG. 6 includes FIGS. 6(a) and (b) for fluorescence signals multiplexed, wherein FIG. 6(a) shows a DMD having mirrors set corresponding to F1 modulated at a first frequency, and mirrors set corresponding to F2 modulated at a second frequency and wherein

DETAILED DESCRIPTION OF THE BEST MODE

Figure 2:
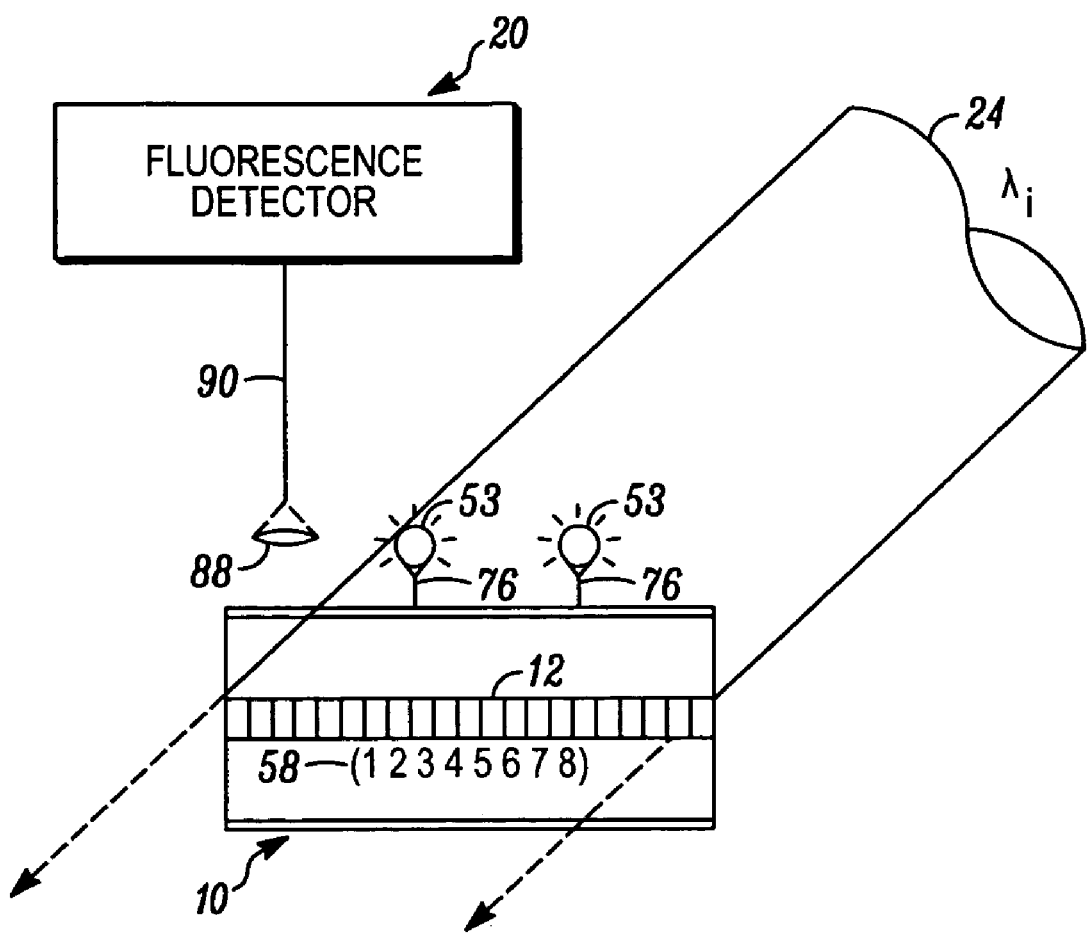
FIG. 2 shows a diagram of a fluorescence detector according to the present invention arranged in relation to a biochip or microarray.

FIG. 2 shows a fluorescence detector 20 according to the present invention arranged in relation to a microbead 10 having a grating 12, consistent with that disclosed in patent application Ser. No. 10/661,234 (WFVA/CyVERA nos. 714-1.27/CV 0038A), filed 12 Sep. 2003, application Ser. No. 10/661,031 (WFVA/CyVERA nos. 714-1.20/CV 0039A), also filed 12 Sep. 2003, which are both assigned to the assignee of the instant application and hereby incorporated by reference in its entirety. The microbead 10 forms part of a so-called "bead based" approach for identifying probes that allows the probes to mix without any specific spatial position, which is often called the "random bead assay" approach. In this approach, the probes are attached to the bead 10 instead of a larger substrate like that discussed above so they are free to move (usually in a liquid medium). This approach has an advantage in that the analyte reaction can be performed in a liquid/solution by conventional wet-chemistry techniques, which gives the probes a better opportunity to interact with the analyte. In operation, this approach requires that each bead or probe be individually identifiable and that different fluorescence spectra be detected on each bead or probe. After the assay process is completed, these uniquely identifying individual beads with attached probes may be aligned on a grid plate and read using the techniques also disclosed in the aforementioned patent applications, and an optical device is used to detect the different fluorescence spectra on each bead or probe that are the result of the assay process. As shown, a light source (not shown) provides light 24 to luminate the microbead 10 to determine the code 58, and the fluorescence detector 20 measures the fluorescence emanating from a "target" analyte 53 attached to a probe 76, consistent with that described in the aforementioned patent applications. The fluorescence detector 86 may also include a lens 88 and an optical fiber 90, as shown, for receiving and providing the fluorescence from the "target" analyte 53 to a fluorescence meter in the fluorescence detector 86. Once the fluorescent microbead 10 is identified and knowing which probe 76 (or single strand of DNA) was attached to each microbead 72, the presence of the "target" analyte 53 may be determined in the assay solution.

The present invention provides a new and unique optical device or scanner having an adaptive spectral filter with a spatial light modulator for detecting the fluorescence spectra on each bead or probe. While the invention is shown and described in relation to the uniquely identifiable microbead 10 disclosed in the aforementioned patent applications, the scope of the invention is clearly intended to include using the technique of the present invention in relation to other devices or media used in assay processes, such as the biochip or microarray, as well as other devices or media either now known or later developed in the future.

Figure 3:
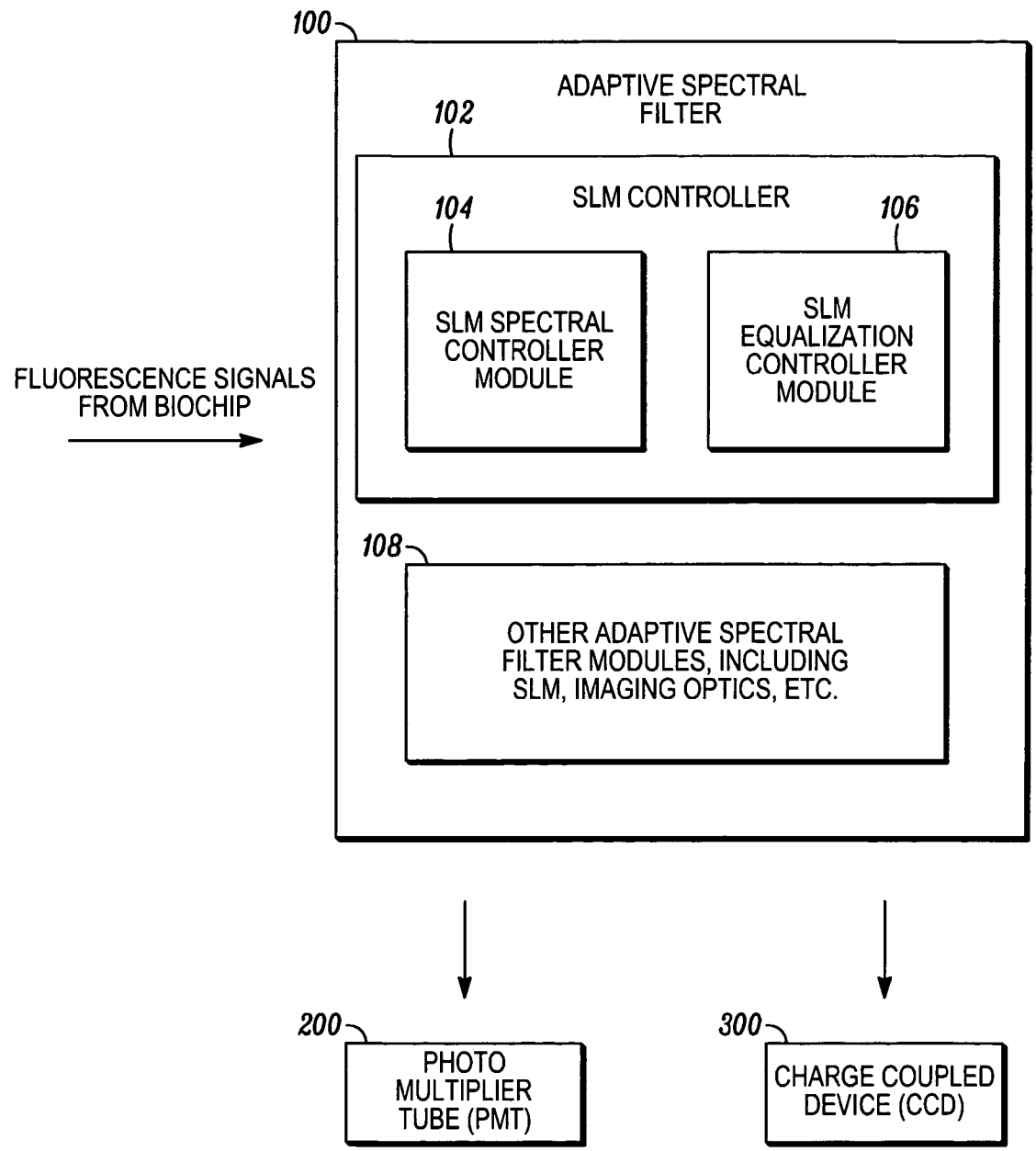
FIG. 3 shows a block diagram of the fluorescence detector shown in FIG. 2.

FIG. 3 shows the adaptive spectral filter 100 arranged in relation to a photo multiplier tube (PMT) 200 and a charge coupled device (CCD) 300. The adaptive spectral filter 100 includes a spatial light modulator (SLM) controller 102 having an SLM spectral controller module 104 and an SLM equalization controller module 106 and also includes other adaptive spectral filter modules or components 108, including a spatial light module, imaging optics etc., which are shown in more detail in FIG. 4. In operation, the SLM spectral controller module 104 detects and processes the fluorescence signal spectrum provided from the device or medium used an assay process, such as microbead 10 shown in FIG. 2. The SLM equalization control module 106 equalizes intensities of the fluorescence signal spectrum across a predetermined portion of the surface of the spatial light modulator (see FIG. 4).

By way of example, and consistent with that described herein, the functionality of the modules 104, 106 may be implemented using hardware, software, firmware, or a combination thereof, although the scope of the invention is not intended to be limited to any particular embodiment thereof. In a typical software implementation, the modules 104, 106 would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation, including to implement such a DMD controller consistent with that shown and described herein to permit the real time control of the fluorescence signal spectrum being monitored, as well as to equalize intensities of the fluorescence signal spectrum across a predetermined portion of the surface of the spatial light modulator, according to the present invention. The scope of the invention is not intended to be limited to any particular implementation using technology now known or later developed in the future. Moreover, the scope of the invention is intended to include the modules 104 and 106 being a stand alone modules, as shown, or in the combination with other circuitry for implementing another module.

Figure 4:
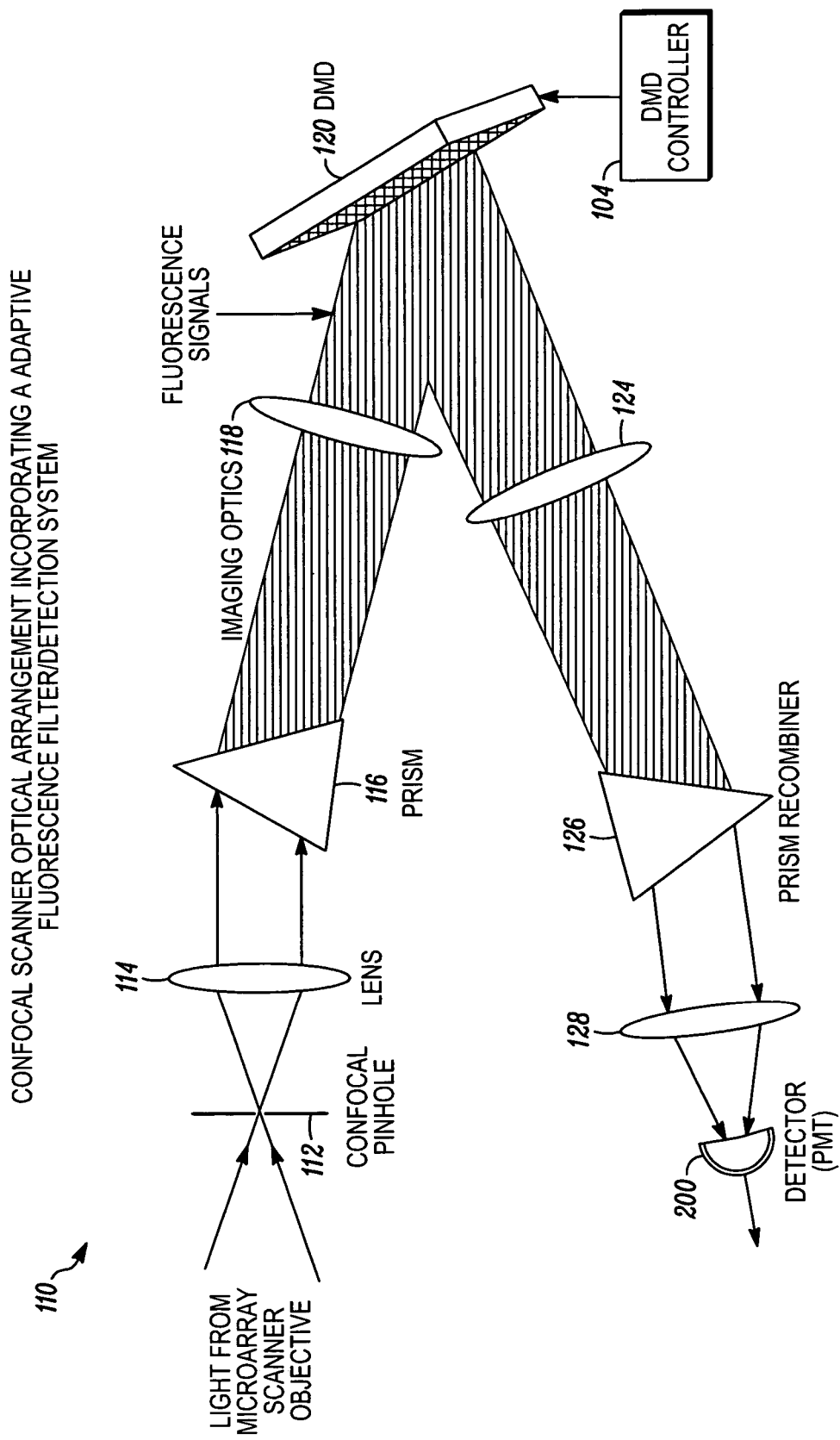
FIG. 4 shows a diagram of a confocal scanner optical arrangement according to the present invention.

FIG. 4: The Confocal Scanner Optical Arrangement 110

FIG. 4 shows one embodiment of a confocal scanner arrangement generally indicated as 110 according to the present invention. The confocal scanner arrangement 110 includes an optical arrangement of the following components: a confocal pinhole 112, a 1st lens 114, a 1st prism 116, the 1st imaging optics 118, the spatial light modulator in the form of a DMD 120, a DMD controller 104 (see FIG. 3), 2nd imaging optics 124, a prism recombiner 126, a 2nd lens 128 and a PMT detector 200 (see FIG. 3). The DMD controller 104 performs the functionality associated with the SLM spectral controller module 104 of the SLM controller 102 of the adaptive spectral filter 100 in FIG. 3. These components will be described in more detail below:

FIGS. 5-7

Figure 6A:
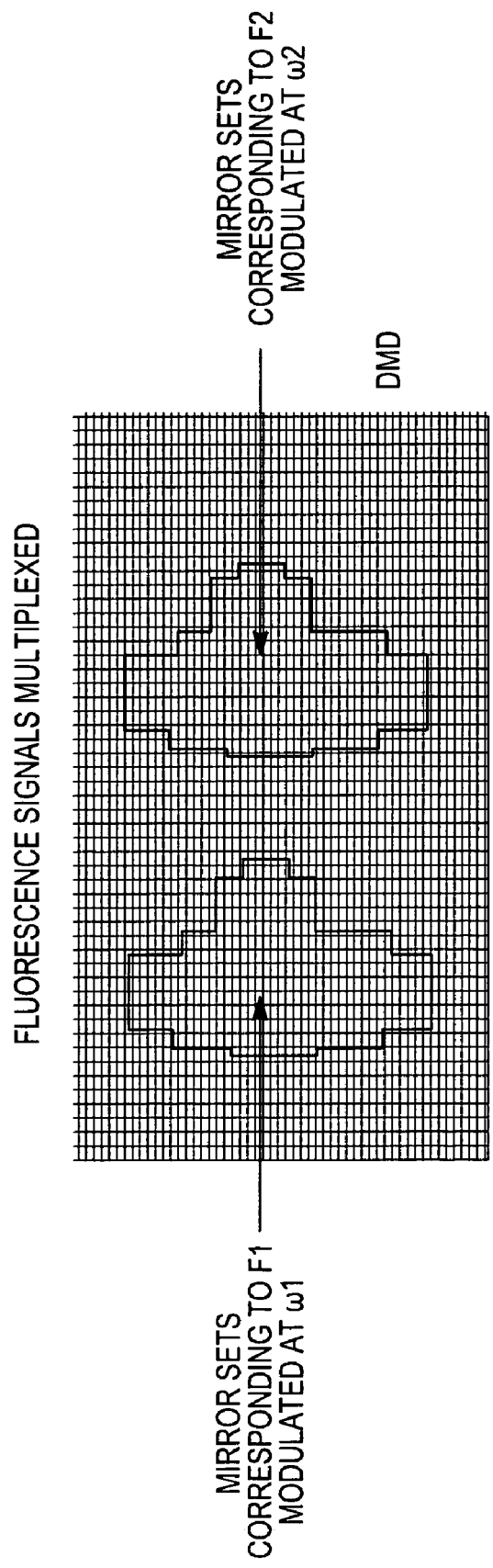
Figure 6B:
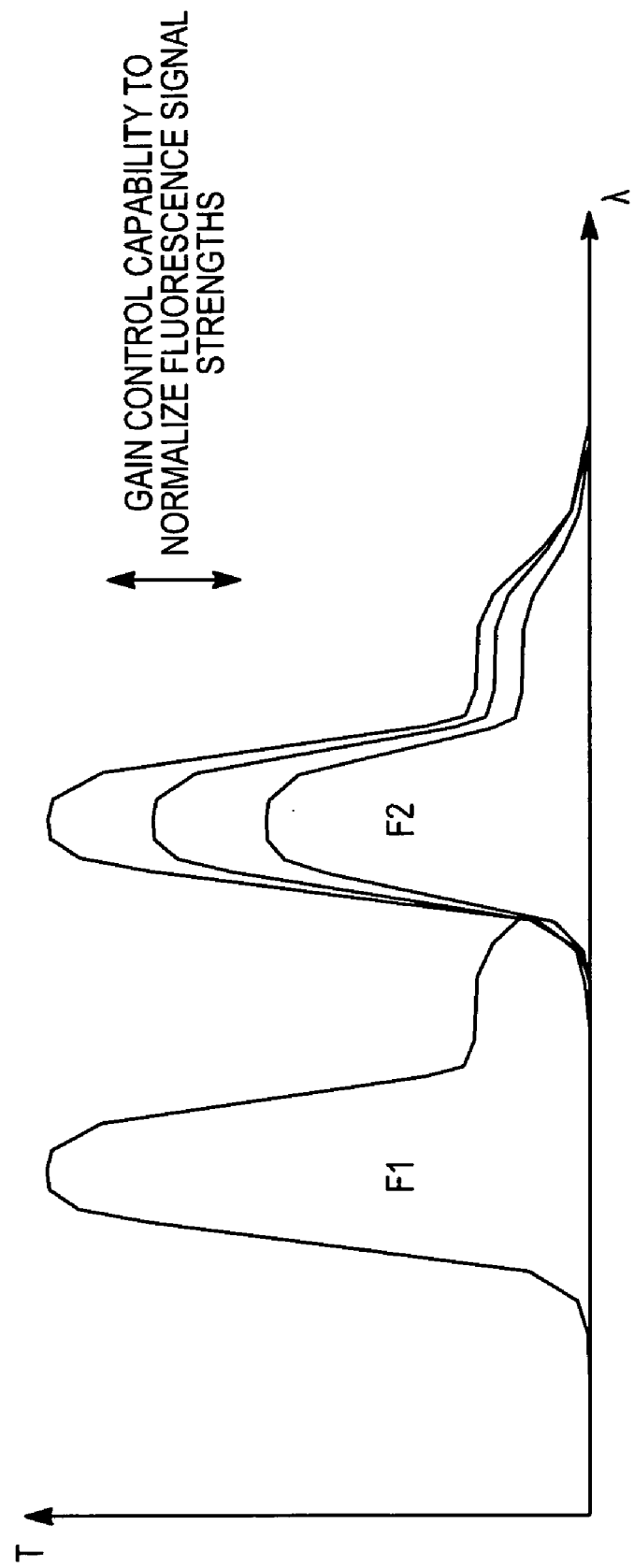
FIG. 6(b) shows a graph of gain control capability to normalize fluorescence signal strengths corresponding to the mirrors set in FIG. 6(a).
Figure 7:
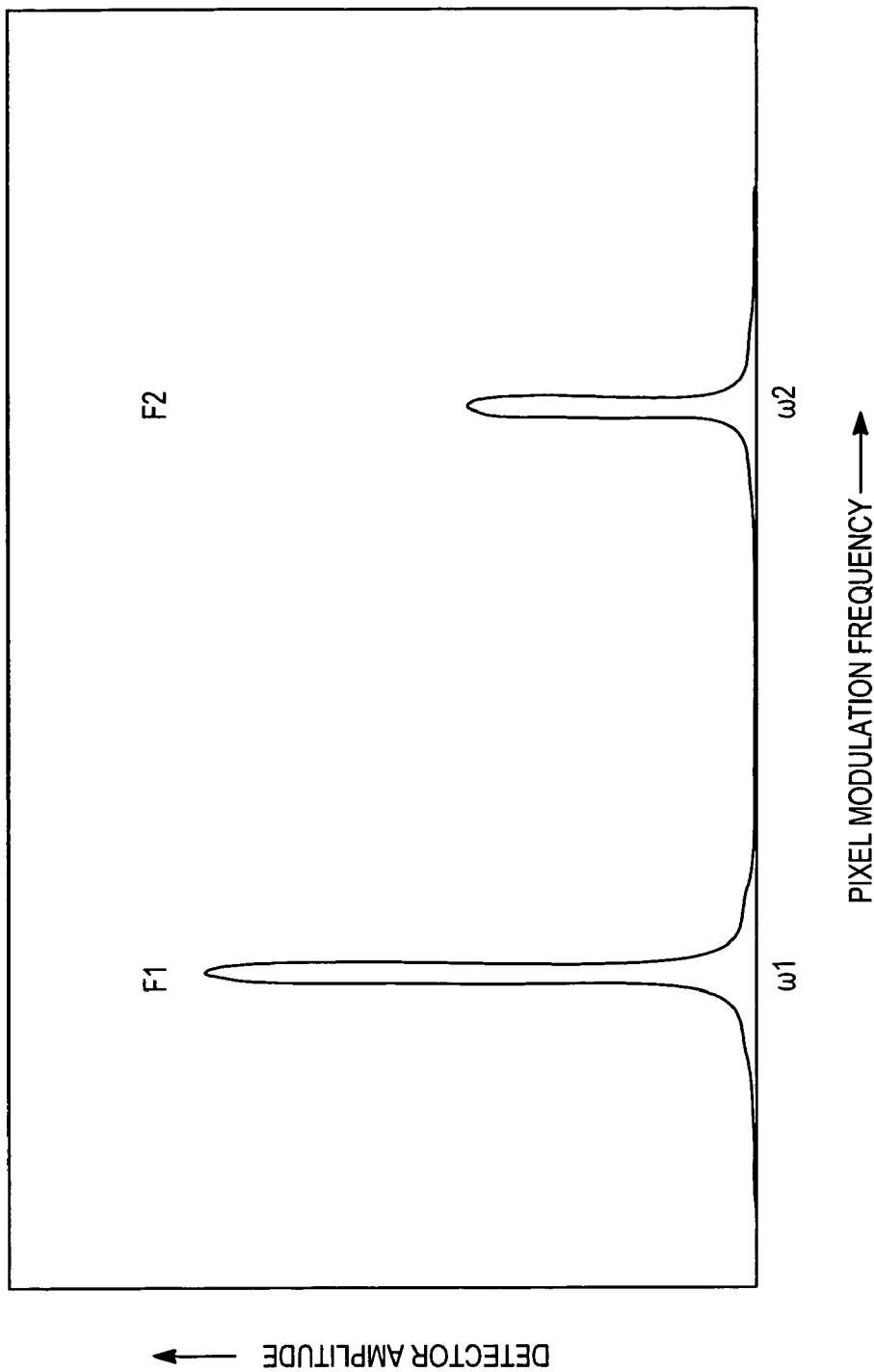
FIG. 7 shows graph of pixel modulated frequency for the operation with multiplexed detection.

FIGS. 5-7 show graphs related to the basic operation of the confocal scanner optical arrangement shown in FIG. 4.

Figure 5A:
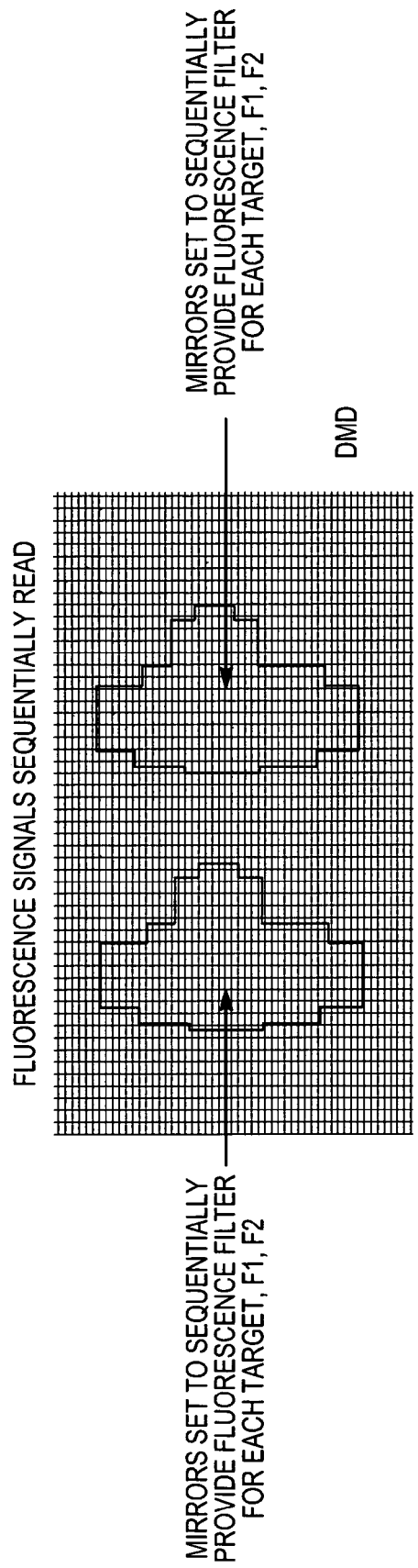
Figure 5B:
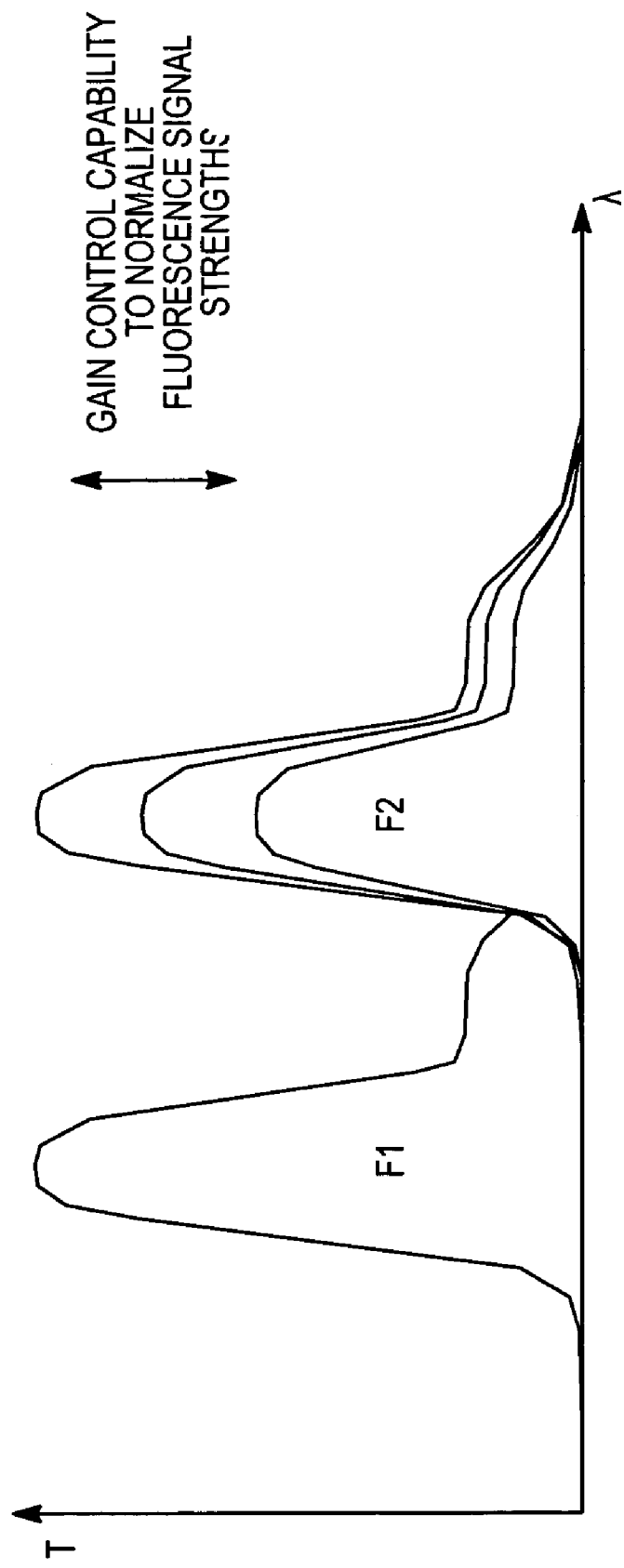
FIG. 5(b) shows a graph of gain control capability to normalize fluorescence signal strengths corresponding to the mirrors set in FIG. 5(a).

For example, FIG. 5 includes FIGS. 5(a) and (b) for fluorescence signals sequentially read, wherein FIG. 5(a) shows a DMD having mirrors set to sequentially provide a fluorescence filter for each target, F1, F2, and wherein FIG. 5(b) shows a graph of gain control capability to normalize fluorescence signal strengths corresponding to the mirrors set in FIG. 5(a).

FIG. 6 includes FIGS. 6(a) and (b) for fluorescence signals multiplexed, wherein FIG. 6(a) shows a DMD having mirrors set corresponding to F1 modulated at a first frequency, and mirrors set corresponding to F2 modulated at a second frequency and wherein FIG. 6(b) shows a graph of gain control capability to normalize fluorescence signal strengths corresponding to the mirrors set in FIG. 6(a).

FIG. 7 shows graph of pixel modulated frequency for the operation with multiplexed detection.

Figure 8:
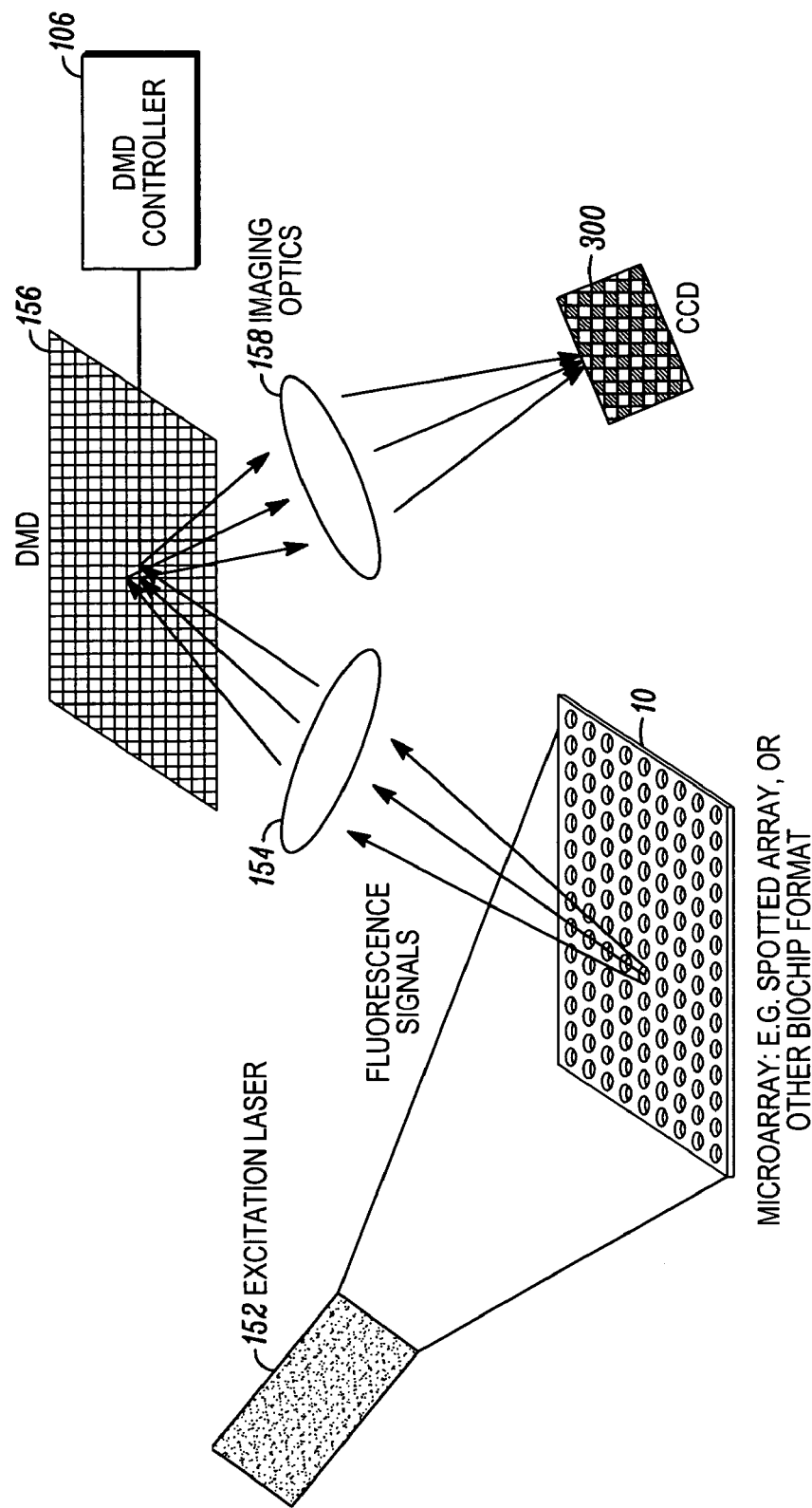
FIGS. 8 and 9 show a DLP spatial light attenuator according to the present invention.
Figure 9:
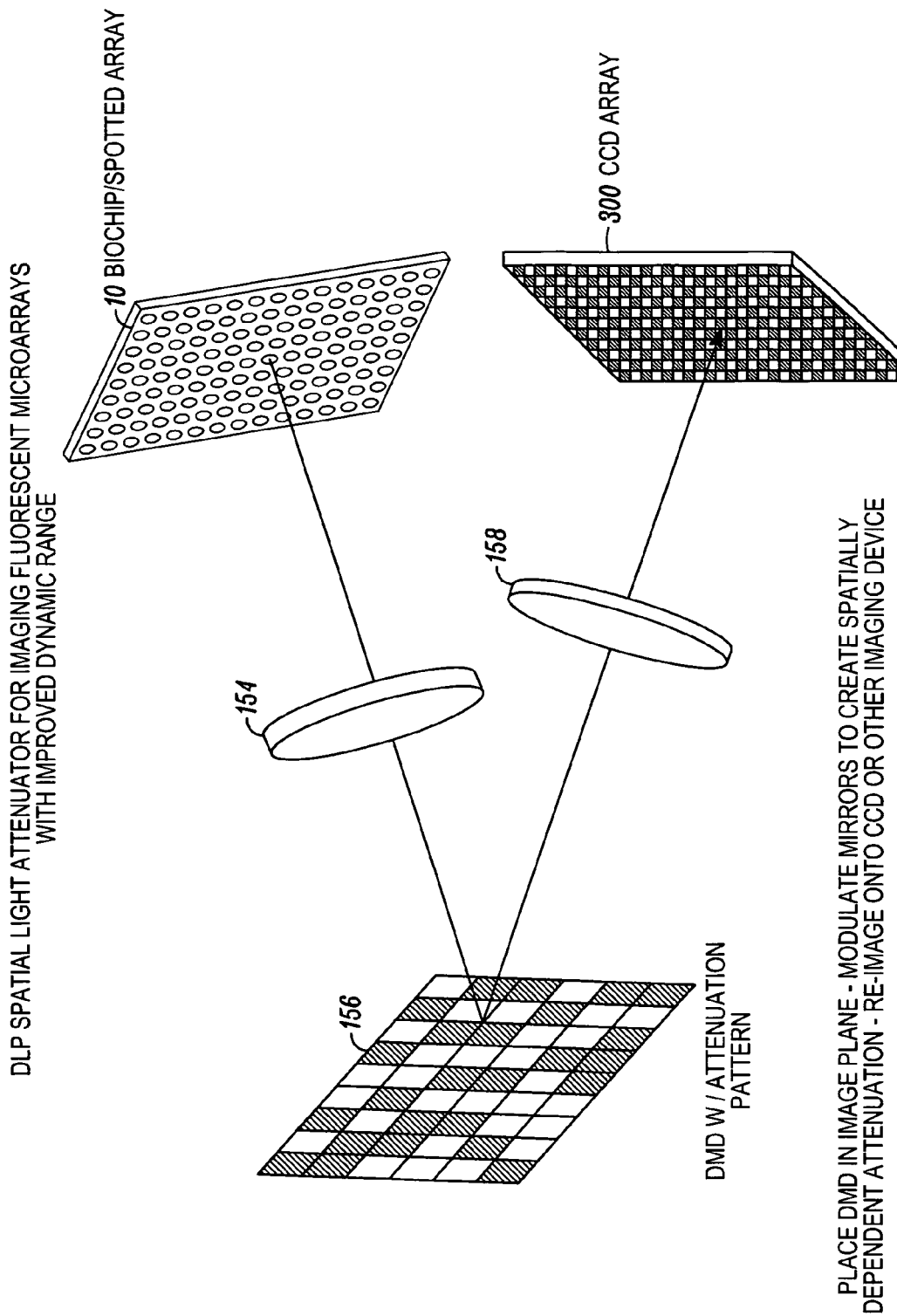

FIGS. 8-9: Equalization

FIGS. 8-9 show an embodiment of the present invention, featuring a digital light processor (DLP) spatial light attenuator generally indicated as 150 for imaging fluorescent microarrays with improved dynamic range. The digital light processor (DLP) spatial light attenuator 150 includes an optical arrangement of the following components: an excitation laser 152, 1st imaging optics 154, a spatial light modulator in the form of a DMD 156, a DMD controller 106 (see FIG. 3), 2nd imaging optics 158 and the CCD 300 (see FIG. 3). The DMD controller 106 performs the functionality associated with the SLM equalization controller module 106 of the SLM controller 102 of the adaptive spectral filter 100 in FIG. 3. According to the present invention, the DMD 156 is placed or arranged in the image plane, the mirrors of the DMD 156 are modulated to create spatially dependent attenuation, the resulting signal is re-imaged onto the CCD 300 or other imaging device.

FIGS. 10-11

Figure 10:
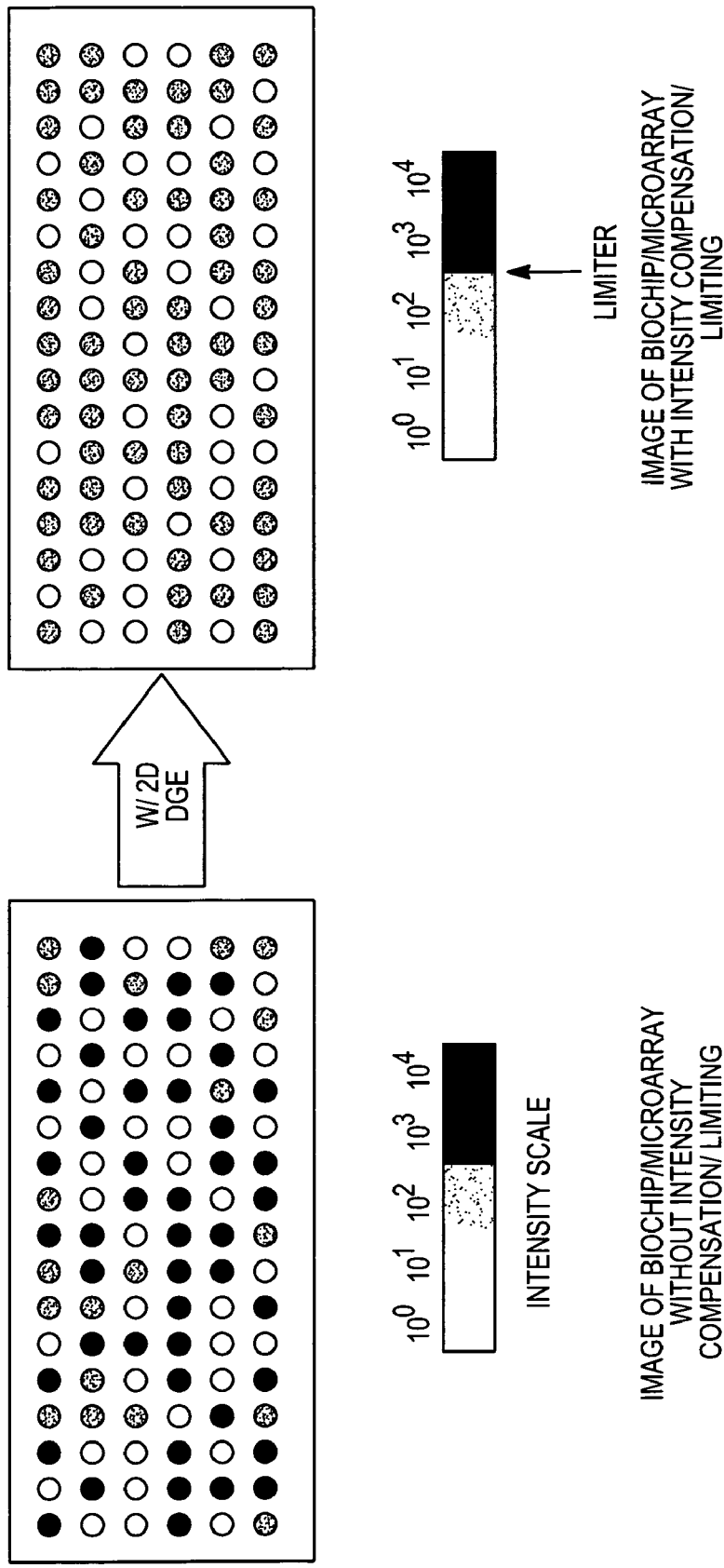
FIGS. 10-11 show comparisons of images of the microarray with and without the equalization feature of the present invention.

FIG. 10 shows a comparison of an image of the biochip/microarray without intensity compensation/limiting versus an image of the biochip/microarray with intensity compensation/limiting (i.e. w/2D digital gain equalization (DGE)), as well as associated intensity scales.

Figure 11:
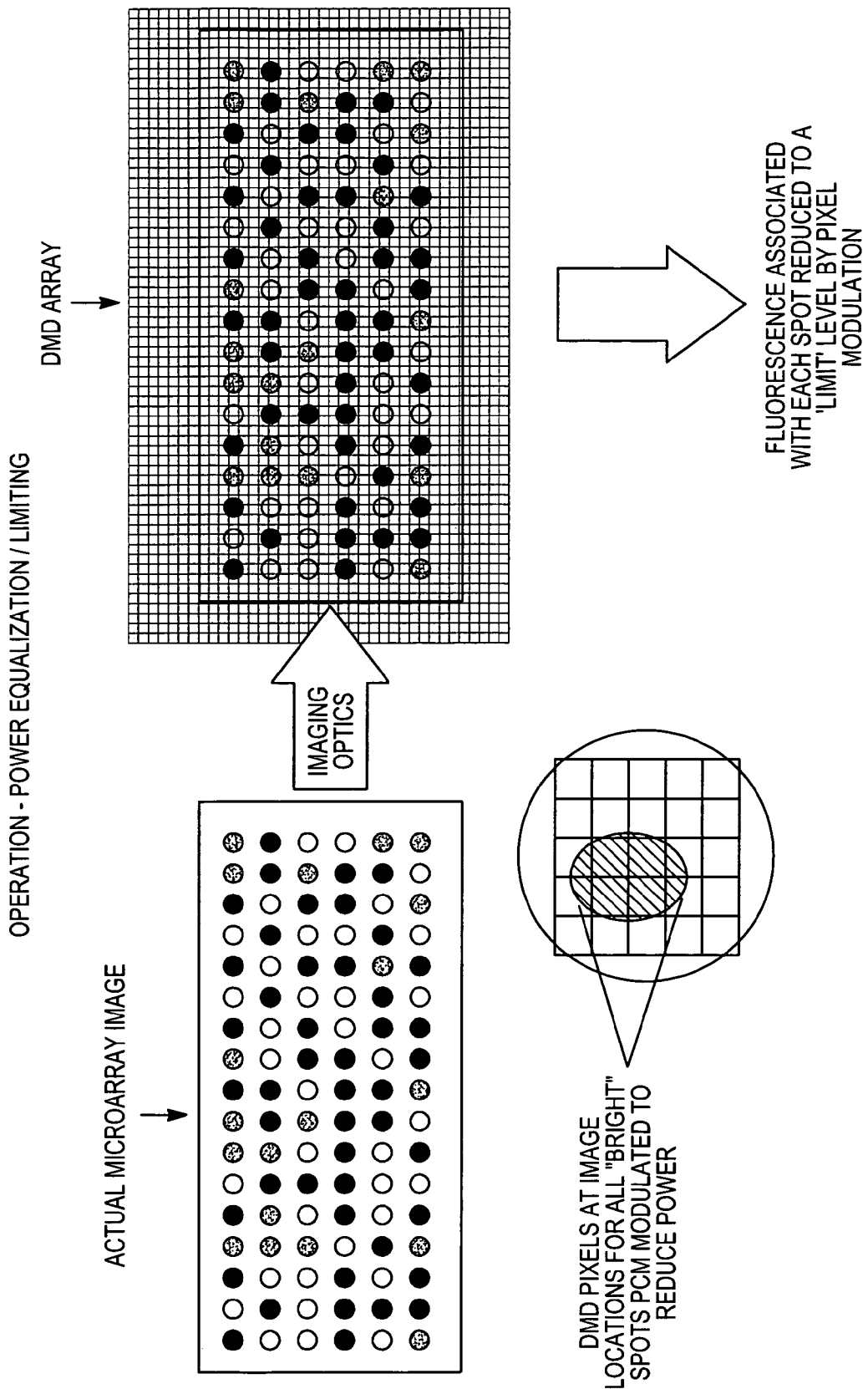

FIG. 11 shows a comparison of an actual microarray image versus an image after being processed by imaging optics and a DMD array. In the later image, the DMD pixels at image locations for all "bright" spots are PCM modulated to reduce power, and the fluorescence associated with each spot is reduced to a "limit" level by pixel modulation.

The Spatial Light Modulator

The spatial light modulation device in the embodiment in FIG. 4 is shown and described as the known Digital Micromirror Device™ (DMD™) manufactured by Texas Instruments, which is described in the white paper entitled "Digital Light Processing™ for High-Brightness, High-Resolution Applications", white paper entitled "Lifetime Estimates and Unique Failure Mechanisms of the Digital Micromirror Device (DMD)", and news release dated September 1994 entitled "Digital Micromirror Display Delivering On Promises of 'Brighter' Future for Imaging Applications", which are incorporated herein by reference. The DMD device is monolithically fabricated by CMOS-like processes over a CMOS memory. Each micro-mirror typically includes, for example, an aluminum mirror, approximately 16 microns square, that can reflect light in one of two directions, depending on the state of the underlying memory cell. Rotation, flipping or tilting of the micromirror is accomplished through electrostatic attraction produced by voltage differences between the mirror and the underlying memory cell. With the memory cell in the "on" (1) state, the micromirror rotates or tilts approximately +10 degrees. With the memory cell in the "off" (0) state, the mirror tilts approximately −10 degrees.

Although the invention has been described as using an array of digital micromirrors to implement the spatial light modulator (SLM) device (or pixelating device) in the embodiments shown herein, it should be understood by those skilled in the art that any SLM that provides pixelated optical signal processing may be used, as described further below.

Further, instead of using micromirrors with two reflective states or angles of reflection (e.g., +/−10 deg) as a pixel that reflects a portion of the light beam, the pixels may have one reflective state and the other state may be absorptive or transmissive. Alternatively, instead of the pixel having at least one state being reflective (which may provide other design advantages), the pixel may have one state being transmissive and the other state being absorptive. Alternatively, the pixel may have two transmissive or partially transmissive states that refract the incoming light out at two different angles. For each of various pixelating devices, the optics surrounding the pixelating device would be changed as needed to provide the same functions as that described for each of the embodiments herein for the different types of pixelated optical signal processing used.

Also, instead of the pixels having a square, diamond or rectangular shape, the pixels may have any other two or three-dimensional shapes, i.e., circle, oval, sphere, cube, triangle, parallelogram, rhombus, trapezoid.

The spatial light modulator in the embodiment in FIGS. 8-9 is shown and described herein as a DLP device; however, the scope of the invention is intended to include other types of light modulator devices. For example, the spatial light modulator may also include a pixelating device, based on, for example, liquid crystal technology, such as a liquid crystal display (LCD). An LCD may provide a device having either one absorptive state and one reflective state, or one absorptive state and one transmissive state. The underlying principle of an LCD is the manipulation of polarized light (i.e., an optical channel). For example, the polarized light may be rotated by 90 degrees in one state of the liquid crystal and not rotated in another state. To provide an LCD having one absorptive state and one transmissive state, a polarizer is provided at each side of the liquid crystal, such that the polarization angles of the polarizers are offset by 90 degrees. A mirror can be added at one end to provide an LCD having one absorptive state and one reflective state.

One example of having a reflective state and a transmissive state is a variation on existing bubble jet technology currently produced by Agilent and Hewlett-Packard Co., and described in U.S. Pat. Nos. 6,160,928 and 5,699,462, respectively. In that case, when the bubble is in one state, it has total internal reflection; and when in the other state, it is totally transmissive. Also in that case, the pixels may not be square but circular or oval.

One example of having a transmissive state and an absorptive state is Heterojunction Acoustic Charge Transport (HACT) Spatial Light Modulator (SLM) technology, such as that described in U.S. Pat. Nos. 5,166,766, entitled "Thick Transparent Semiconductor Substrate, Heterojunction Acoustic Charge Transport Multiple Quantum Well Spatial Light Modulator", Grudkowski et al. and 5,158,420, entitled "Dual Medium Heterojunction Acoustic Charge Transport Multiple Quantum Well Spatial Light Modulator" to Grudkowski et al., provided the material used for the HACT SLM will operate at the desired operational wavelength. In that case, the pixels may be controlled by charge packets that travel along a surface acoustic wave that propagates along the device, where the size of the charge controls the optical absorption.

The Implementation of the Other Optical Components

The confocal pinhole 112, the 1st lens 114, the 1st prism 116, the 1st imaging optics 118, the 2nd imaging optics 124, the prism recombiner 126, the 2nd lens 128, as well as the excitation laser 152, the 1st imaging optics 154, the 2nd imaging optics 156 are all optical devices that are known in the art, and the scope of the invention is not intended to be limited to any particular type or kind thereof.

Moreover, the other adaptive spectral filter modules or components 108, as well as the photo multiplier tube (PMT) 200 and the charge coupled device (CCD) 300, are also all optical devices that are known in the art, and the scope of the invention is not intended to be limited to any particular type or kind thereof.

The Scope of the Invention

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

Moreover, it should also be understood that, unless stated otherwise herein, any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein without departing from the spirit and scope of the present invention.

The invention claimed is:

1. An optical device or scanner for monitoring fluorescence signals emitted from a surface of a medium, the fluorescent signals varying in intensity across the surface, the optical device or scanner comprising:
    an adaptive spectral filter including a spatial light modulator that selectively modulates the fluorescent signals, the spatial light modulator modulating the fluorescent signals emitting from at least one spatial location of the surface based upon an intensity of the fluorescent signals emitting from the corresponding spatial location, wherein the optical device or scanner records an image using multiple fluorescence tags that indicate a degree of binding or hybridization of target biomolecules to probes immobilized on the medium which is used in an assay process, and wherein the adaptive spectral filter is controlled to be spectrally matched to a first fluorescent signal spectrum and is then adjusted to be spectrally matched to a second fluorescent signal spectrum that is different from the first fluorescent signal spectrum.

2. An optical device or scanner according to claim 1, wherein the adaptive spectral filter detects the fluorescence signal spectrum provided from the medium used in an assay process.

3. An optical device or scanner according to claim 1, wherein the adaptive spectral filter has an SLM equalization control module that equalizes intensities of the fluorescence signal spectrum across a predetermined portion of the surface of the spatial light modulator.

4. An optical device or scanner according to claim 1, wherein the spatial light modulator comprises an array of selectively controllable micromirrors.

5. An optical device or scanner according to claim 1, wherein the spatial light modulator comprises at least one of a reflective and a transmissive element.

6. An optical device or scanner according to claim 1, wherein the spatial light modulator is a pixelating device.

7. An optical device or scanner according to claim 1, wherein the optical device or scanner is an imaging biochip/microarray confocal scanner.

8. An optical device or scanner according to claim 1 wherein the medium includes a plurality of microbeads or a microarray.

9. An optical device or scanner according to claim 1 wherein the spatial light modulator attenuates the fluorescent signals associated with the corresponding spatial location when the intensity of the fluorescent signals of the corresponding spatial location exceeds a predetermined value.

10. An optical device or scanner according to claim 1 wherein the surface comprises a first spatial location and a second spatial location adjacent to the first spatial location, the spatial light modulator modulating an intensity of the fluorescent signals emitting from the first spatial location when the intensity of the fluorescent signals from the first spatial location is different from an intensity of the fluorescent signals emitting from the second spatial location.

11. A method for monitoring fluorescence signals emitted from a surface of a medium, the fluorescent signals varying in intensity across the surface, the method comprising:
  positioning an adaptive spectral filter to receive the fluorescent signals emitted from the medium, the spectral filter comprising a spatial light modulator; and
  selectively modulating the fluorescent signals emitted from the surface of the medium with the spatial light modulator, the fluorescent signals emitted from at least one spatial location of the surface being modulated based upon an intensity of the fluorescent signals emitted from the corresponding spatial location;
  recording, at the optical device or scanner, an image using multiple fluorescence tags that indicate a degree of binding or hybridization of target biomolecules to probes immobilized on the medium which is used in an assay process;
  controlling the adaptive spectral filter to be spectrally matched to a first fluorescent signal spectrum: and
  adjusting the adaptive spectral filter to be spectrally matched to a second fluorescent signal spectrum that is different from the first fluorescent signal spectrum.

12. A method according to claim 11, wherein the method includes detecting the fluorescence signal spectrum provided from the medium used in an assay process with the adaptive spectral filter.

13. A method according to claim 11, wherein the method includes equalizing intensities of the fluorescence signal spectrum across a predetermined portion of the surface of the spatial light modulator with an SLM equalization control module in the adaptive spectral filter.

14. A method according to claim 11, wherein the spatial light modulator comprises an array of selectively controllable micromirrors.

15. A method according to claim 11, wherein the spatial light modulator comprises at least one of a reflective and a transmissive element.

16. A method according to claim 11, wherein the spatial light modulator is a pixelating device.

17. A method according to claim 11, wherein the spatial light modulator is used in an imaging biochip/microarray confocal scanner.

18. A method according to claim 11, further comprising recording an image using multiple fluorescence tags that indicate a degree of binding or hybridization of target biomolecules to probes immobilized on the medium.

* * * * *

UNITED STATES PATENT AND TRADEMARK OFFICE
CERTIFICATE OF CORRECTION

PATENT NO. : 7,602,952 B2  Page 1 of 1
APPLICATION NO. : 11/281937
DATED : October 13, 2009
INVENTOR(S) : Kersey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 970 days.

Signed and Sealed this

Fifth Day of October, 2010

David J. Kappos
*Director of the United States Patent and Trademark Office*